US008553953B2

(12) United States Patent
Lee et al.

(10) Patent No.: US 8,553,953 B2
(45) Date of Patent: Oct. 8, 2013

(54) ENDOSCOPIC NAVIGATION METHOD AND ENDOSCOPIC NAVIGATION SYSTEM

(75) Inventors: Tsung-Chun Lee, Taipei (TW); Syu-Jyun Peng, Zhubei (TW); Hsuan-Ting Chang, Xinying (TW); Hsiu-Po Wang, Taipei (TW)

(73) Assignee: National Yunlin University of Science and Technology, Yunlin (TW)

( * ) Notice: Subject to any disclaimer, the term of this patent is extended or adjusted under 35 U.S.C. 154(b) by 567 days.

(21) Appl. No.: 12/821,091

(22) Filed: Jun. 22, 2010

(65) Prior Publication Data
US 2011/0160534 A1    Jun. 30, 2011

(30) Foreign Application Priority Data

Dec. 31, 2009  (TW) ............................... 98146317 A

(51) Int. Cl.
*G06K 9/00*   (2006.01)
*G06K 9/46*   (2006.01)

(52) U.S. Cl.
USPC ............................ 382/128; 382/165; 382/190

(58) Field of Classification Search
None
See application file for complete search history.

(56) References Cited

U.S. PATENT DOCUMENTS

| | | | | |
|---|---|---|---|---|
| 4,916,533 A | * | 4/1990 | Gillies et al. ................... 348/65 |
| 5,956,416 A | * | 9/1999 | Tsuruoka et al. ............. 382/128 |
| 6,671,405 B1 | * | 12/2003 | Savakis et al. ................ 382/203 |
| 7,894,648 B2 | * | 2/2011 | De Groen et al. ............ 382/128 |
| 2005/0010082 A1 | * | 1/2005 | Nishimura et al. ........... 600/145 |
| 2006/0002626 A1 | * | 1/2006 | Matsumoto ................... 382/276 |
| 2006/0015011 A1 | * | 1/2006 | Hasegawa et al. ............ 600/117 |
| 2006/0050966 A1 | * | 3/2006 | Nishimura et al. ........... 382/209 |
| 2007/0053557 A1 | * | 3/2007 | Cahill et al. .................. 382/128 |
| 2008/0253686 A1 | * | 10/2008 | Bayer .......................... 382/284 |
| 2008/0292154 A1 | * | 11/2008 | Nishimura et al. ........... 382/128 |
| 2009/0010551 A1 | * | 1/2009 | Matsuda ....................... 382/228 |
| 2009/0041320 A1 | * | 2/2009 | Tanaka ......................... 382/128 |

(Continued)

OTHER PUBLICATIONS

Liu, D., Cao, Y., Tavanapong, W., Wong, J., Oh, J.H., and de Groen, P.C., Quadrant Coverage Histogram: A New Method for Measuring Quality of Colonoscopic Procedures, 2007, Proceedings of the 29th Annual International Conference of the IEEE EMBS, pp. 3470-3473.*

*Primary Examiner* — Stephen R Koziol
*Assistant Examiner* — Jonathan S Lee

(57) ABSTRACT

An endoscopic navigation method includes the steps of: receiving an image from an endoscopic navigation system; performing image classification to determined whether the image is usable; performing a first image process on the image to filter out dark areas of the image to produce a first processed image; performing a first determination procedure to identify the dark areas of the first processed image; producing a first result image for indicating lumen direction; performing a second image process to filter out fold curves of the image to produce a second processed image when there is no dark area in the image; performing a second determination procedure to identify the fold curves of the second processed image; producing a second result image for indicating lumen direction according to the fold curves; and outputting the first or the second result image to a display device to assist users in operating the photographic device.

17 Claims, 16 Drawing Sheets

(56) References Cited

U.S. PATENT DOCUMENTS

| | | | |
|---|---|---|---|
| 2009/0074268 A1* | 3/2009 | Tanaka et al. | 382/128 |
| 2009/0148017 A1* | 6/2009 | Inoue et al. | 382/128 |
| 2009/0220133 A1* | 9/2009 | Sawa et al. | 382/128 |
| 2009/0225158 A1* | 9/2009 | Kimoto | 348/77 |
| 2009/0252390 A1* | 10/2009 | Matsuzaki et al. | 382/128 |
| 2010/0034436 A1* | 2/2010 | Kono | 382/128 |
| 2010/0046816 A1* | 2/2010 | Igual-Munoz et al. | 382/128 |
| 2010/0119110 A1* | 5/2010 | Kanda | 382/103 |
| 2010/0124365 A1* | 5/2010 | Kanda | 382/128 |
| 2010/0183204 A1* | 7/2010 | Kanda | 382/128 |
| 2010/0204547 A1* | 8/2010 | Tanaka et al. | 600/145 |
| 2010/0208047 A1* | 8/2010 | Kitamura | 348/65 |
| 2010/0316273 A1* | 12/2010 | Inoue et al. | 382/128 |
| 2011/0069876 A1* | 3/2011 | Kanda | 382/134 |

* cited by examiner

ENDOSCOPIC NAVIGATION METHOD AND ENDOSCOPIC NAVIGATION SYSTEM

CROSS REFERENCE TO RELATED APPLICATION

This Application claims priority of Taiwan Patent Application No. 098146317, filed on Dec. 31, 2009, the entirety of which is incorporated by reference herein.

BACKGROUND OF THE INVENTION

1. Field of the Invention

The present invention relates to an endoscopic navigation method, and an endoscopic navigation system.

2. Description of the Related Art

More and more electronic video apparatuses are being applied in the field of colonoscopy, due to advanced development for image and electronic monitors. Specifically, electronic video devices, such as micro charge-coupled devices, are able to retrieve colored images from a colon. An electronic video endoscope is used to quantify and estimate of the health of a colon. Following image capturing by the electronic video endoscope, computer-aided diagnosis is performed to evaluate important features of the images. One significant feature of a colon sought by doctors is a lumen boundary, which is usually an abnormality in the colon. A doctor often determines the direction of a lumen according to a colon video, wherein expertise is used to manipulate an endoscope. Generally, various flecks appear on the dark area of an endoscopic video image and a lot of fold curves are scattered between the lumens and the intestinal walls. When the lumens are not in a homogenous region, there may be bright reflections from one of the intestinal walls, which make it difficult for the electronic video apparatuses to retrieve lumen border images.

There are several light sources at the tip of the endoscope used to illuminate the interior of a colon. Due to distance limitations, illumination of the surfaces of intestinal walls closer to the light sources is brighter than those further from the light sources. Consequently, the darker areas are usually in the direction or the region of the lumen. Meanwhile, the lumen region is not static. The lumen region changes according to size and shape of the lumen, background luminance and reflection characteristics etc., such that it is difficult for doctors to accurately judge the direction of the lumen. Furthermore, curves and bent portions of a colon adds to difficulty in identify the lumen by blurring images of the lumen. Note also, that if the insertion of an endoscope dose not follows the direction of the lumen, the tip of the endoscope may rub against the intestinal walls of a patient so that the patient feels uncomfortable.

Therefore, in order to solve the problems described above, the present invention provides an endoscopic navigation method and an endoscopic navigation system using a specific image process.

BRIEF SUMMARY OF INVENTION

A detailed description is given in the following embodiments with reference to the accompanying drawings. The object of the present invention is to provide a method for adjusting displayed navigation direction using sensors and a navigation device using the same.

The present invention provides an endoscopic navigation method. The method comprises the steps of: receiving an image from a photographic device of a endoscopic navigation system in a lumen; performing image classification to determine whether the image is usable; performing a first image process on the image to filter out dark areas of the image to produce a first processed image; performing a first determination procedure to identify the dark areas of the first processed image; producing a first result image for indicating lumen direction; performing a second image process to filter out fold curves of the image to produce a second processed image when there is no dark area in the image; performing a second determination procedure to identify the fold curves of the second processed image; producing a second result image for indicating lumen direction according to the fold curves; outputting the first result image or the second result image to a display device in the endoscopic navigation system to assist a user in operating the photographic device in the lumen.

The present invention further provides an endoscopic navigation system, comprising: a photographic device, for photographing a colon interior; an image classifying module, for retrieving an image photographed by the photographic device, and performing image classification to determine whether the image is usable; a first image process module, for performing a first image process on the image to filter out dark areas of the image to produce a first processed image, performing a first determination procedure to identify the dark areas of the first processed image, and producing a first result image for indicating lumen direction according the dark areas; a second image processing module, for performing a second image process on the image to produce a second processed image, performing a second determination procedure to filter out fold curves to identify the fold curves of the second processed image and producing a second result image for indicating lumen direction according to the fold curves; and a display device, for displaying the first result image or the second result image to assist a user in operating the photographic device in the lumen.

The present invention analyzes colon images by image processing algorithm to accurately determine colon lumen direction in a patient according to darkness and brightness of colon images and characteristics of colon folds; hence a user can be correctly guided to operate a camera of an endoscopic navigation system. Thus, a doctor, when conducting clinical diagnosis and treatment, can smoothly insert the endoscope and manipulate it according to indication of analyzed images, so that discomfort of a patient is at a minimal.

BRIEF DESCRIPTION OF DRAWINGS

The present invention can be more fully understood by reading the subsequent detailed description and examples with references made to the accompanying drawings, wherein:

FIGS. 4A-1~4A-2 is a flowchart illustrating steps of performing the first determination procedure of the endoscopic navigation method of the present invention;

DETAILED DESCRIPTION OF INVENTION

The following description is of the best-contemplated mode of carrying out the invention. This description is made for the purpose of illustrating the general principles of the invention and should not be taken in a limiting sense. The scope of the invention is best determined by reference to the appended claims.

Figures 1, 4A:
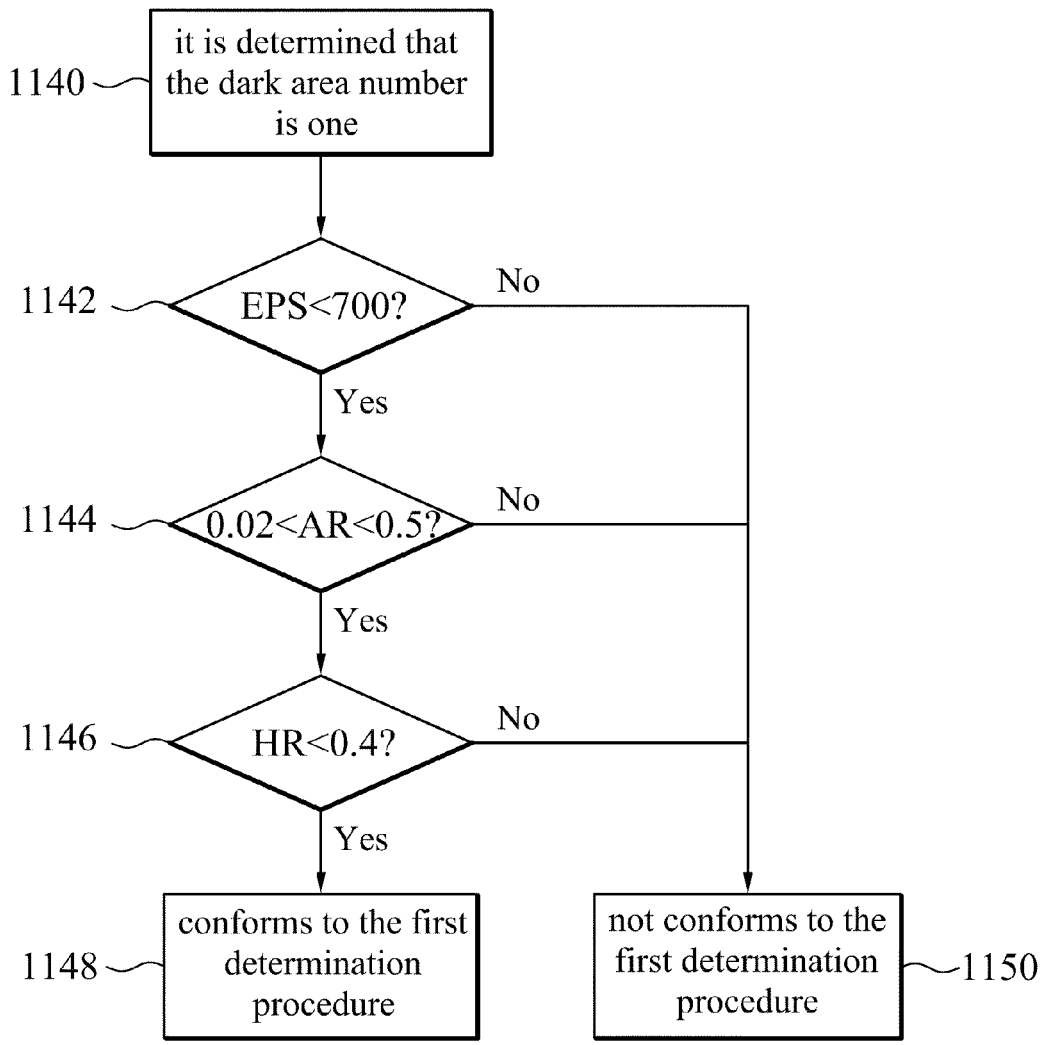
Figures 2, 4A:
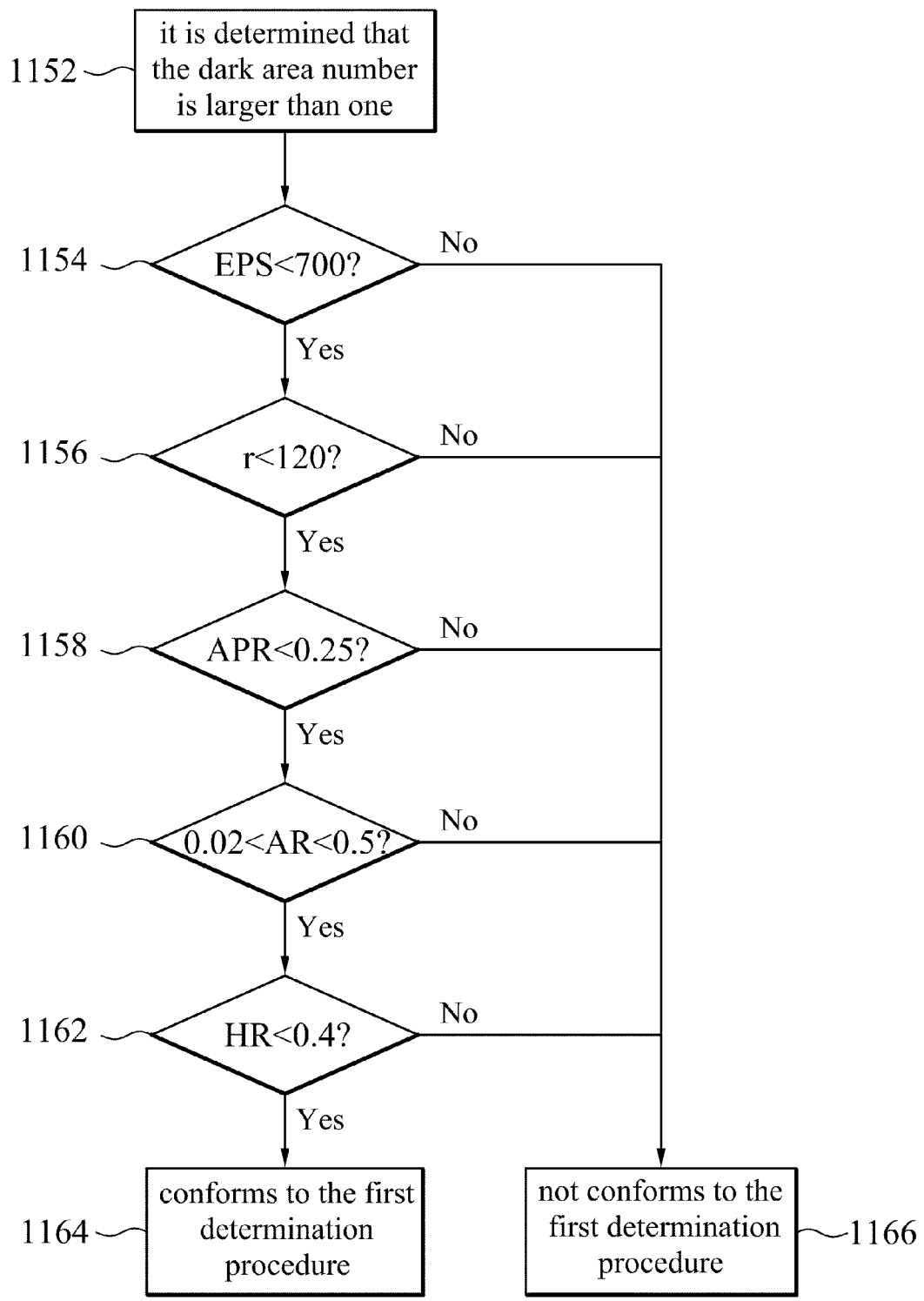

FIG. 1 is a flowchart 100 illustrating an endoscopic navigation method of the present invention. In an embodiment, a plastic colon model that simulates real colons is used. The inside structure of the colon model is inspected by an endoscopic instrument and then a video recording is taken. The video recording is divided into image portions of the colon. Then the images are further analyzed to determine lumen direction. Generally speaking, a doctor manipulates an endoscopic camera according to colon images displayed by a display device of an endoscopic system. Clinically, the method of the present invention is able to receive real time images, to analyze images in real time and show images in real time such that a doctor may accurately quickly guide and operate the camera of the endoscopic navigation system.

The flowchart 100 details a method to analyze real time images of a patient's colon for the purpose of guiding users to smoothly operate the endoscopic navigation system. In step 102, an image of the lumen is received from a photographic device or camera inserted into the colon such as micro charge-coupled device. The image is one of a series of images transformed to from a real time video. In step 104, image classification is performed. Note that there are various types of images due to different photographic positions and angles of a camera. Generally there are four categories of images which are: very bright image, very dark image, double-exposure image and clear image. An image is classified according to its parameters such as hue, saturation and luminance values in a specified color space such as an HSV color space. In the embodiment, users may set parameter ranges used for image classification of the above four categories.

Figure 1A:
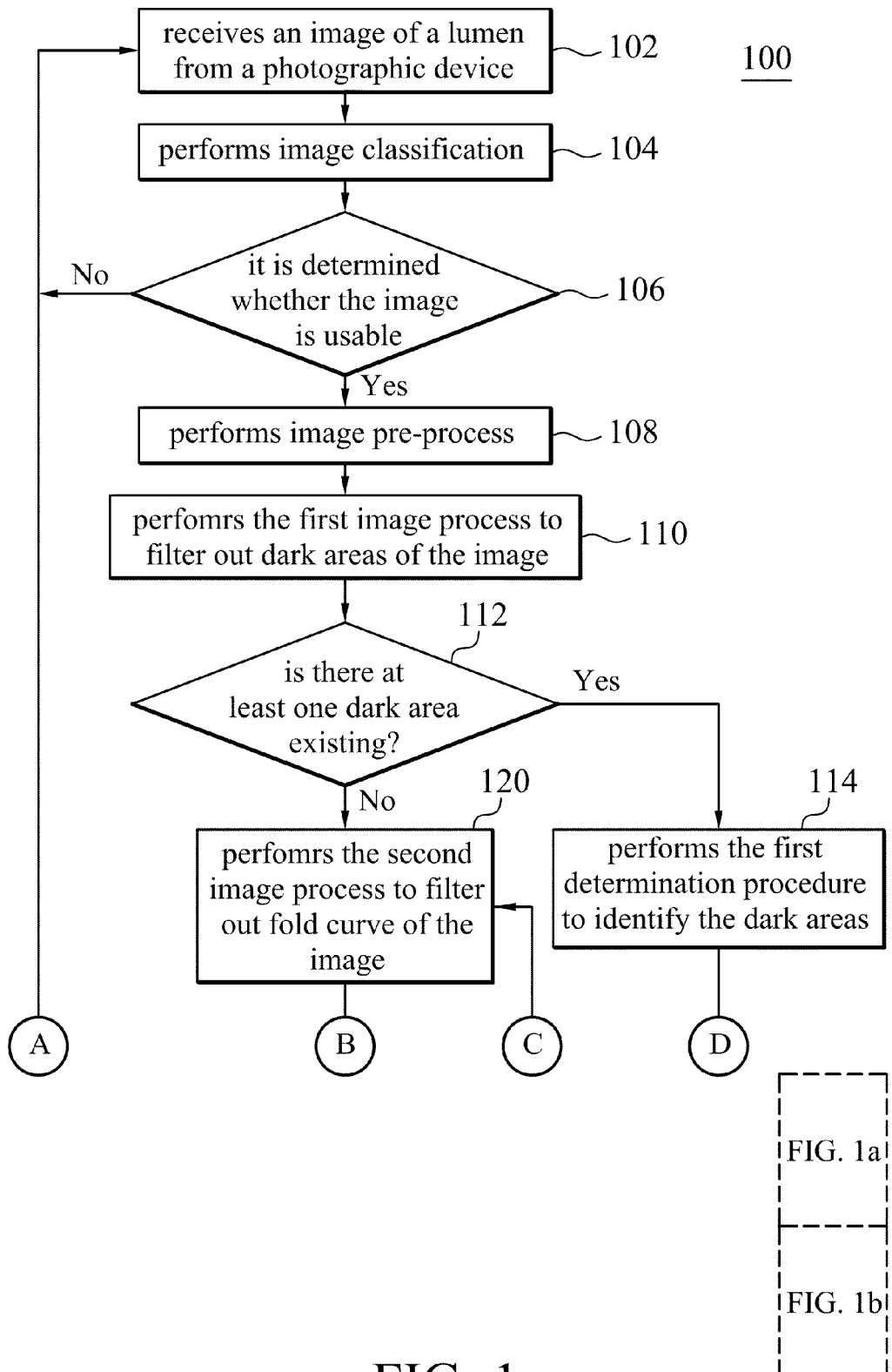
FIGS. 1a~1b is a flowchart illustrating an endoscopic navigation method of the present invention.
Figure 1B:
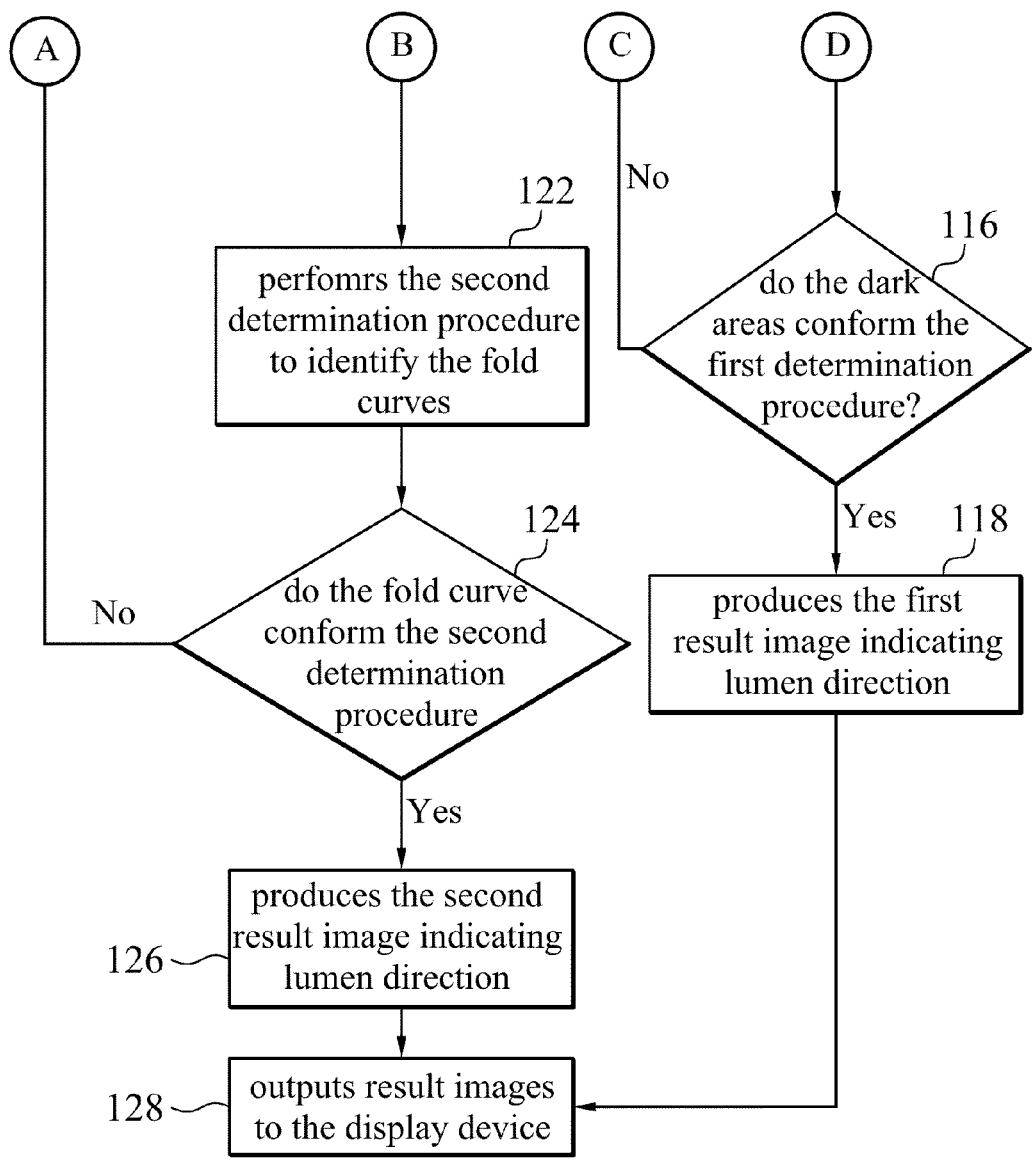
Figure 2:
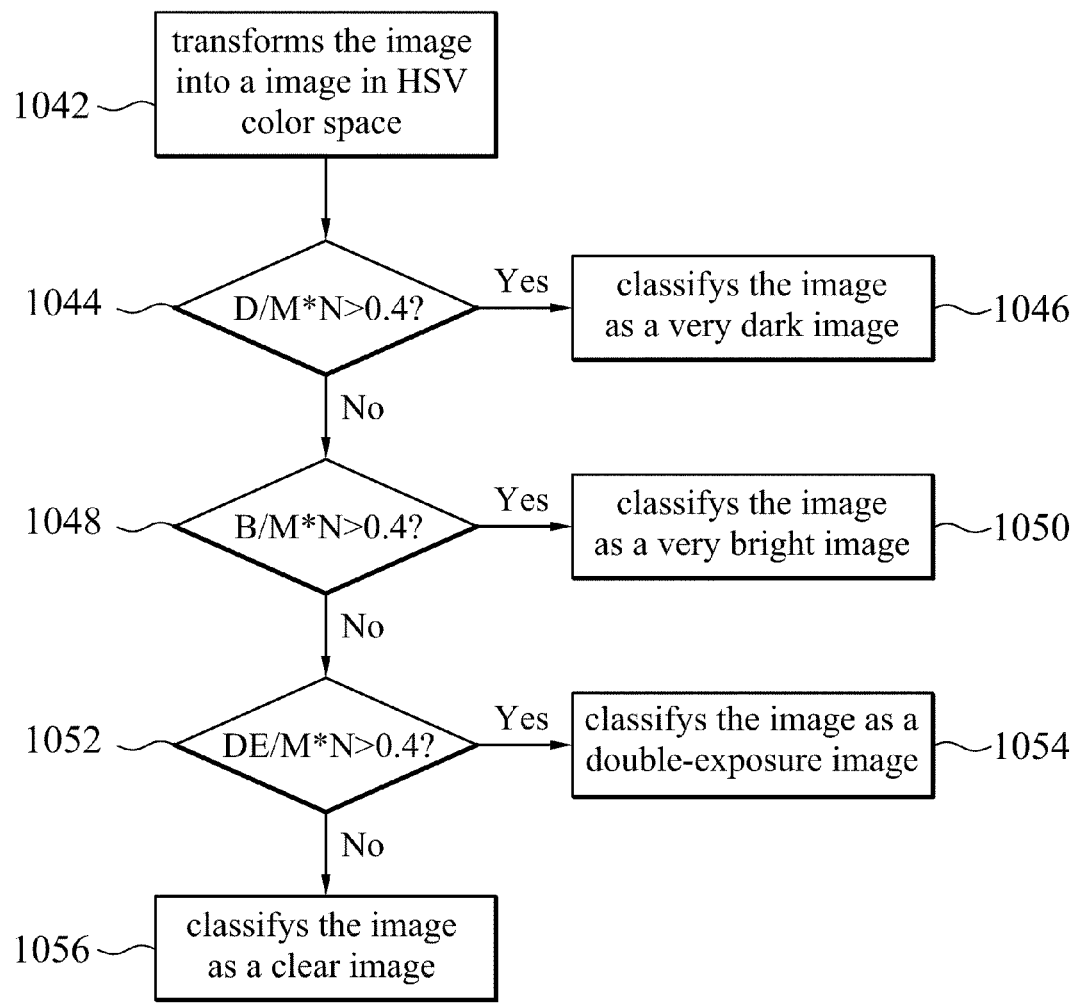
FIG. 2 is a flowchart illustrating steps of performing image classification of the endoscopic navigation method of the present invention.

A more detailed classification procedure is shown in FIG. 2. In step 1042, a retrieved image is transformed into a color space other than its original color space. For example, an image in RGB color space is transformed into an image in HSV color space. A first order classification is performed in step 1044. For example, when a ratio of pixels in the image with luminance values smaller than a first predetermined luminance value to the image size (M*N), is larger than a predetermined ratio value, the image is classified as a very dark image. In the embodiment, the first predetermined luminance value is set as a 0.22 unit, and the predetermined ratio value is set as 0.4. That is, when pixels with luminance smaller than the 0.22 unit exceed 40 percent of the image, the image is classified as a very dark image and the image is not usable.

The second order classification is performed in step 1048. For example, when a ratio of pixels in the image with luminance values larger than a second predetermined luminance value to the image size (M*N), is larger than the predetermined ratio value, the image is classified as a very bright image. In the embodiment, the second predetermined luminance value is set as a 0.7 unit, and the predetermined ratio value is still 0.4. That is, when pixels with luminance larger than a 0.7 unit exceed 40 percent of the image, the image is classified as a very bright image and the image is not usable.

The third order classification is performed in step 1052. For example, when a ratio of a number DE of pixels in the image with hue values smaller than a first predetermined hue value or larger than a second predetermined hue value, and saturation values larger than a predetermined saturation value to the image size, is larger than the predetermined ratio value, the image is classified as a double-exposure image. In the embodiment, the first predetermined hue value is set as a 0.01 unit, the second predetermined hue value is set as a 0.1 unit, and the predetermined saturation value is set as a 0.75 unit. That is, when the number of pixels with hue values smaller than the 0.01 unit and saturation value larger than the 0.75 unit, or with hue values larger than 0.1 unit and saturation value larger than 0.75 unit exceeds 40 percent of the image, the image is classified as double-exposure image and the image is not usable.

Finally, when the image is not classified as a very dark image, very bright image or double-exposure image, the image is classified as a clear image. After the selection of the classification procedure, if the mages are not classified as being not usable, the images are classified as clear image. When the images are usable, a further image process is executed.

Figure 3A:
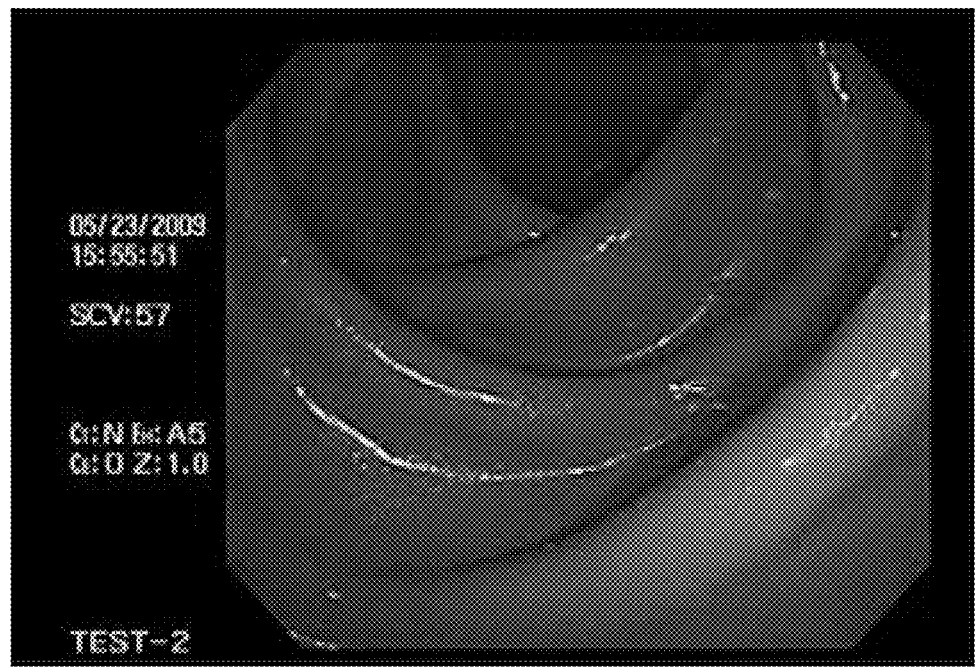
FIG. 3A is a non-processed image in an embodiment of the present invention.
Figure 3B:
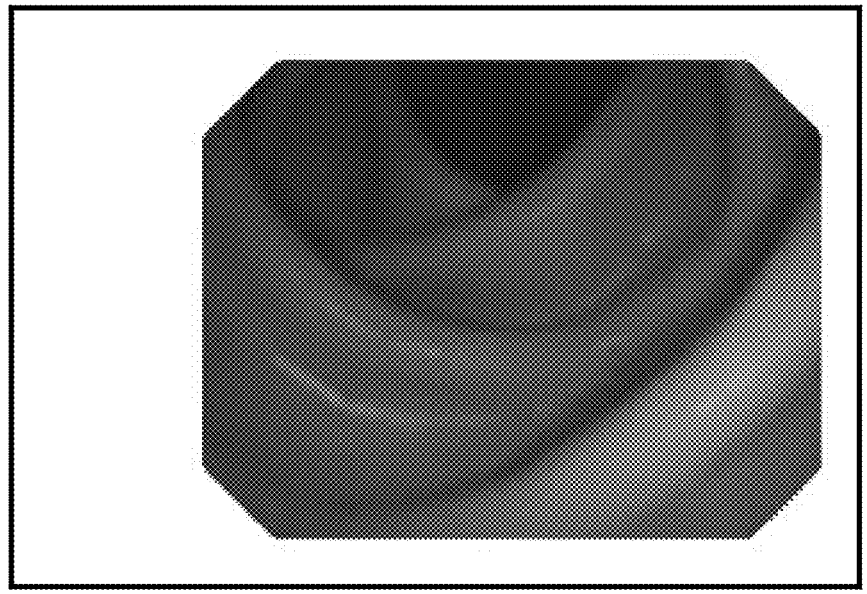
FIG. 3B is a pre-processed image in an embodiment of the present invention.

Return to FIG. 1, after image classification 104, if the image is usable, step 108 is performed. In step 108, an image pre-process is performed. The main purpose of the image pre-process is to filter out and intensify a portion of the image with a structure of the lumen. FIG. 3A is a non-processed image. FIG. 3B is a pre-processed image. The image pre-process procedure includes gray-level transformation, average filtering and masking.

Figure 3C:
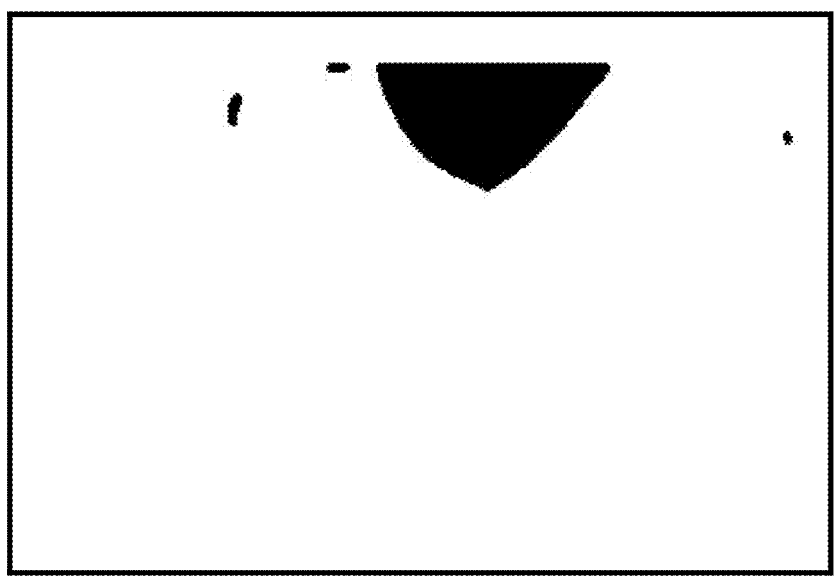
FIG. 3C is a first processed image in an embodiment of the present invention.

Referring again to FIG. 1, in step 110, a first image process is performed. The main purpose of performing the first image process is to filter out dark areas of the image for identification during a subsequent determination procedure. The first image process includes binarization, labeling filtering and median filtering processes which are performed on the image in FIG. 3B. The image in FIG. 3C is processed by the first image process. The image luminance of the colon lumen is relatively darker than that of the colon lumen's surrounding portion. A median filtering process can be performed to filter out small area and intensify darkness of lumen regions. Labeling filtering is used to count the number of dark areas. In the embodiment, the number of dark areas is four according to the first processed image as shown in FIG. 3C.

After the first image process is performed, in step 110, it is determined whether there is a dark area in the first image. If no, then step 120 is performed. If yes, then step 114 is performed.

Figure 4B:
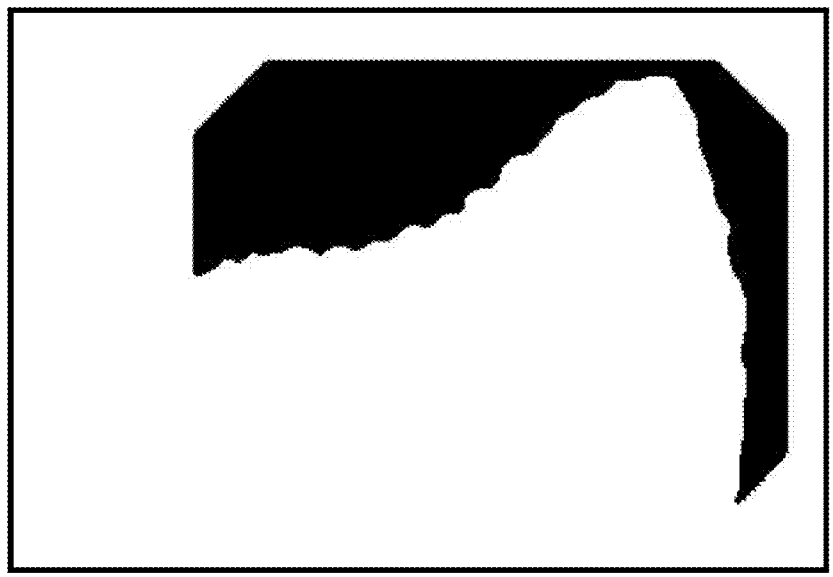
FIG. 4B is an image that does not conform with the first determination procedure in another embodiment of the present invention.

In step 114, the first determination procedure is performed to identify dark areas of the image. Step 114 is shown in FIG. 4A. When the number of dark areas is one, it is determined whether the boundary pixel number (EPS) is smaller than a predetermined pixel number. In the embodiment, the predetermined pixel number is set at 700. In one embodiment, as the image shows in FIG. 4B, a boundary pixel is 876, which is larger than 700. Thus, the image does not conform to the first determination procedure. If the boundary pixel number was smaller than 700, then whether a ratio (AR) of the dark area to the first processed image area is within a predetermined ratio range would be determined. In the embodiment, the predetermined ratio range is set between 0.02 and 0.5. That is, when the dark area is not within a 2% and 50% ratio range of the image area, the first determination procedure is determined to not be conformable. If the dark area percentage is within the 2% and 50% ratio range, then whether a ratio (HR) of pixels of the dark area with hue values within a predetermined hue value range to the dark area is smaller than a predetermined hue area ratio would be determined. In the embodiment, the predetermined hue value range is 0-1, and the predetermined hue area ratio is 0.4. That is, when pixels of the dark areas with hue values within 0-1 is smaller than 40% of the dark area, the first determination procedure is determined to be a complete conformability.

Figure 4C:
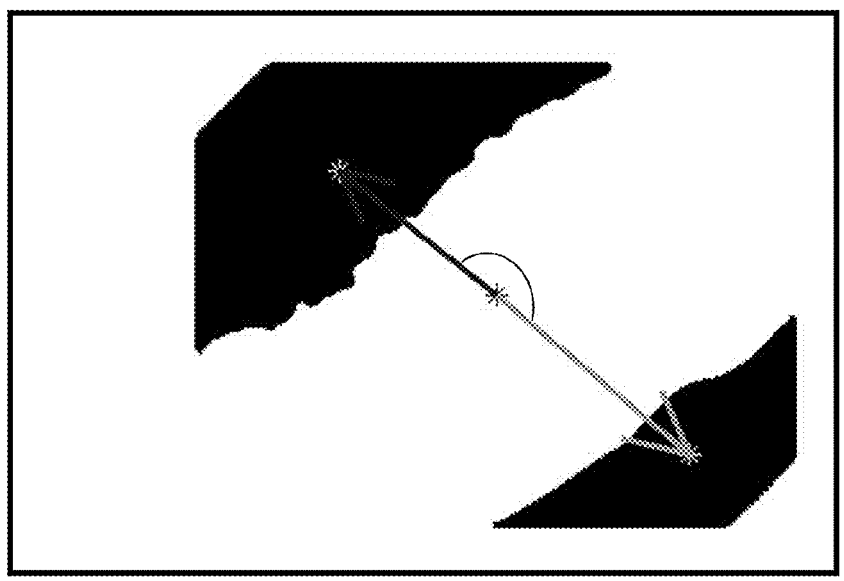
FIG. 4C is an image that does not conform with the first determination procedure in another embodiment of the present invention.

Furthermore, a different determination procedure is performed when the number of dark areas is larger than one as compared to when the number of dark areas is one. First, it is determined whether boundary pixel number of the dark areas is smaller than a predetermined pixel number. In the embodiment, the predetermined pixel number is set at 700. As FIG. 3C shows, boundary pixel number of all the dark areas is smaller than 700. Next, it is determined whether an included angle r between the first largest dark area and the second largest dark area in the processed image is smaller than a predetermined angle. In one embodiment, as FIG. 4C shows, the included angle between the two dark areas is larger than 120 degree, so the first determination procedure is determined as not being conformable. If a match is determined, such as the dark areas shown in FIG. 3C, then it is determined whether a ratio (APR) of the second largest dark area to the first largest dark area is smaller than a predetermined ratio value. In the embodiment, the predetermined ratio is set at 0.25. That is, when the second largest dark area is smaller than 25% of the first largest dark area, the determination condition is determined as being conformable, as the image shows in FIG. 3C.

Next, it is determined whether a ratio of the dark areas to the first processed image area is within a predetermined ratio range. In the embodiment, the predetermined ratio range is set between 0.02 and 0.5. That is, when the percentage of the dark areas is within 2% and 50% of the image area, the determination procedure is determined to be conformable. Next, it is determined whether a ratio (HR) of the dark areas with hue values within a predetermined hue value range to the all dark areas is smaller than a predetermined hue area ratio. In the embodiment, the predetermined hue value range is 0-1 and the predetermined hue area ratio is 0.4. That is, when pixels of the dark areas with hue values within 0-1 is smaller than 40% of the total dark areas, the first determination procedure is determined to be a complete match, otherwise, the first determination is determined to not be a match.

When the first determination procedure is a match, as the image shows in FIG. 3C, step 118 is performed. Otherwise, step 120 is performed, which is the second image process.

Figure 5A:
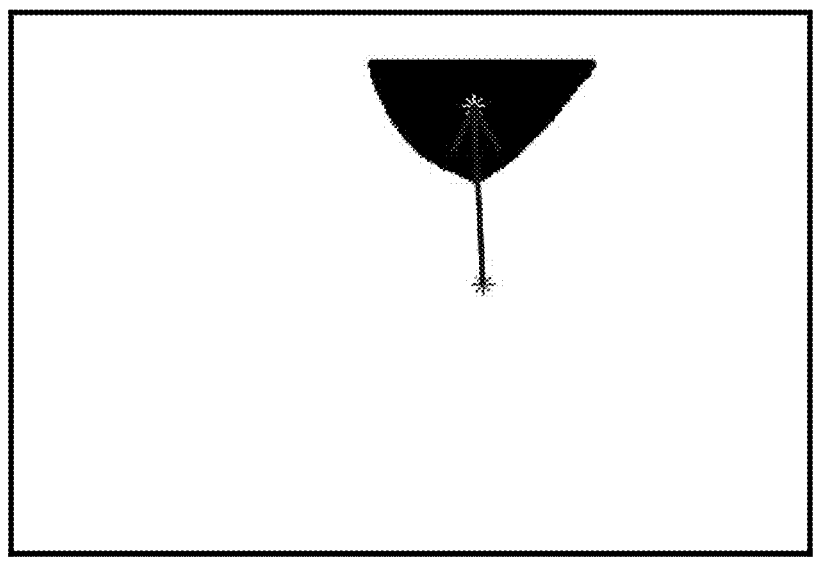
FIG. 5A is an image that conforms with the first determination procedure producing an indicative symbol in an embodiment of the present invention.
Figure 5B:
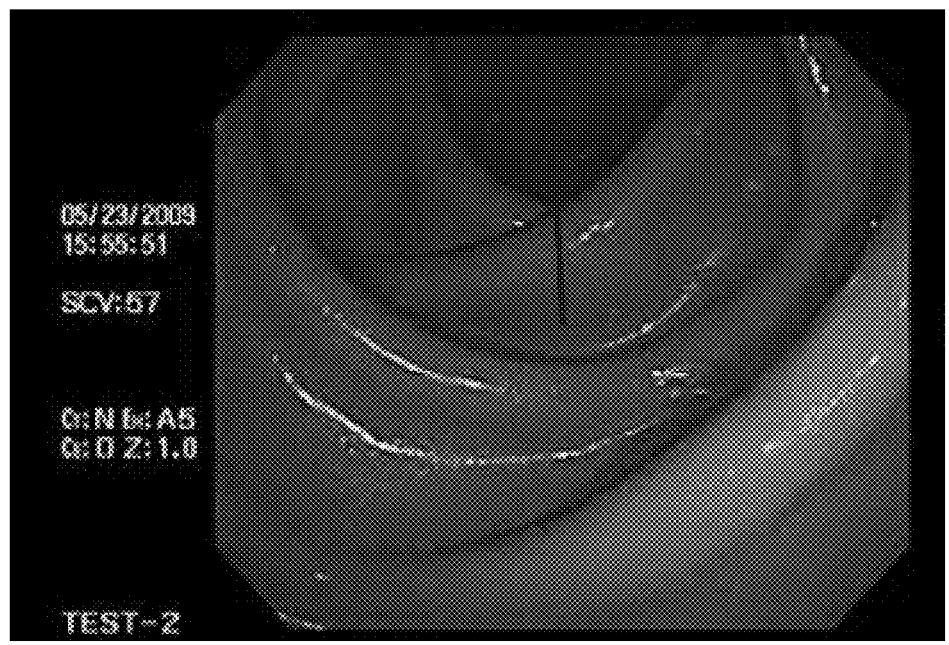
FIG. 5B is a first result image with an indicative symbol in an embodiment of the present invention.

Referring to FIG. 1 again, in step 118, a first result image indicating lumen direction is produced. After the first determination procedure, the dark area of the image may be a lumen region of the colon. Next, the geometrical center of the dark area, namely center of the lumen, is determined. If there is a plurality of dark areas, then the center is calculated according to the largest dark area. An indicative symbol is generated from the center of the image such as an arrow, which points to the center of the dark area as FIG. 5A shows. The position and direction of the indicative symbol is mapped to the original image, and then a result image is formed with an indicative direction as FIG. 5B shows. The direction which the arrow points to is the lumen region.

Figure 6A:
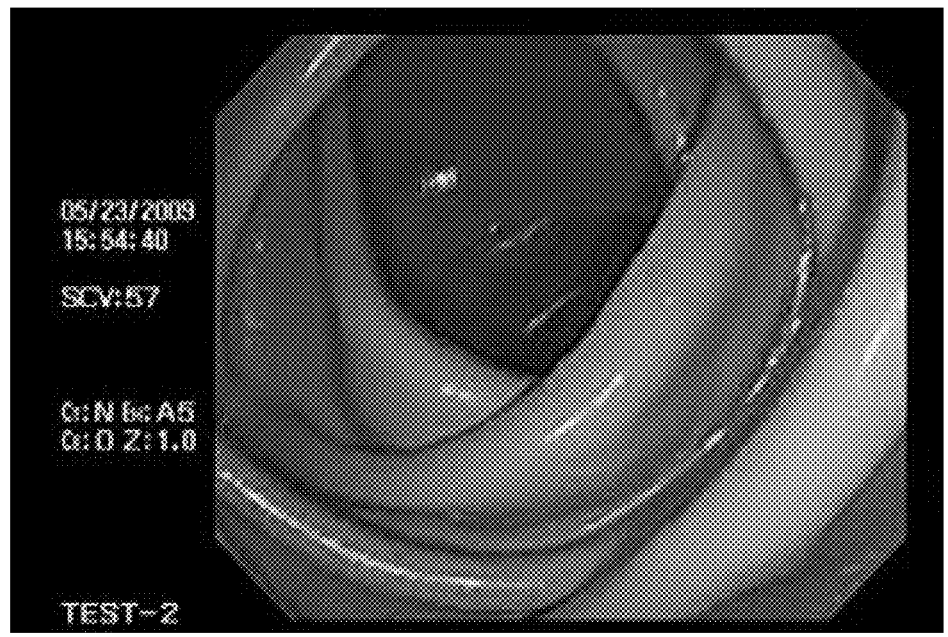
FIG. 6A is a non-processed image in an embodiment of the present invention.
Figure 6B:
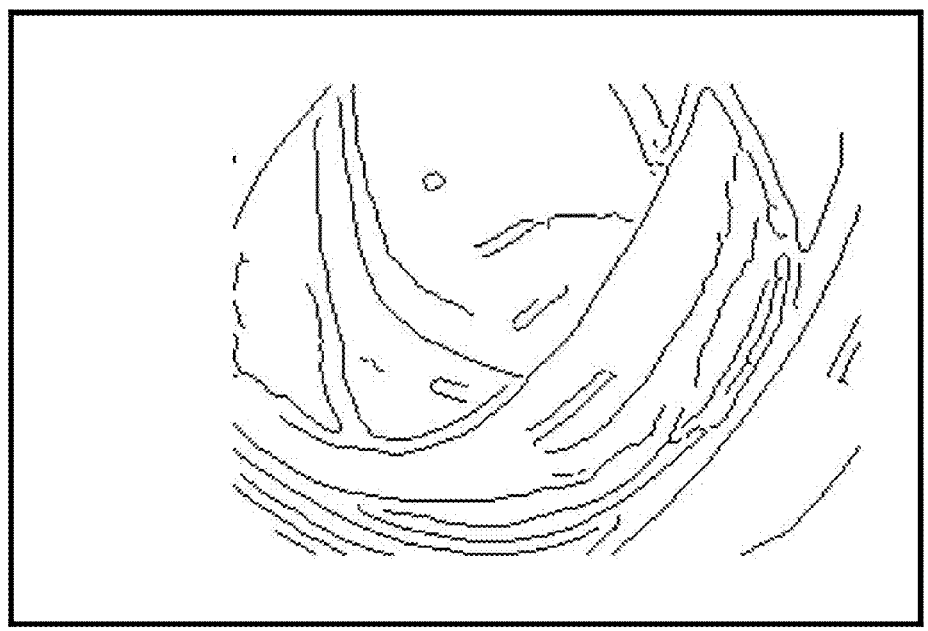
FIG. 6B is a second processed image being pre-processed in an embodiment of the present invention.

The above-mentioned darkness detection algorithm does not necessarily accurately determine the lumen direction. Clinically, a doctor, given years of training and experience, further utilizes colon folds to determine a lumen region. Generally speaking, the direction vertical to the direction of a colon fold is the direction of lumen region. Thus, the fold detection algorithm is developed according to the characteristics of the colon folds. Referring to FIG. 1, when there is no dark area in the image or the determination procedure is determined as not matching, step 120 is performed. In step 120, the second image process is performed. The main purpose of step 120 is to filter out fold curves in the image. The second image process includes Laplace filtering, Canny edge detection, edge mask and labeling filtering, as FIGS. 6A-6B shows. FIG. 6A is a non-processed image, and FIG. 6B is an image after performing an image pre-process and first image process. The Laplace filtering intensifies the fold contrast, Canny edge detection can detect all possible fold curves, and edge masking can get rid of endoscopic image edges to obtain independently unique colon fold images. Finally, the fold curve number and curve lengths are determined with label filtering. Next, step 122 is performed.

Figure 7:
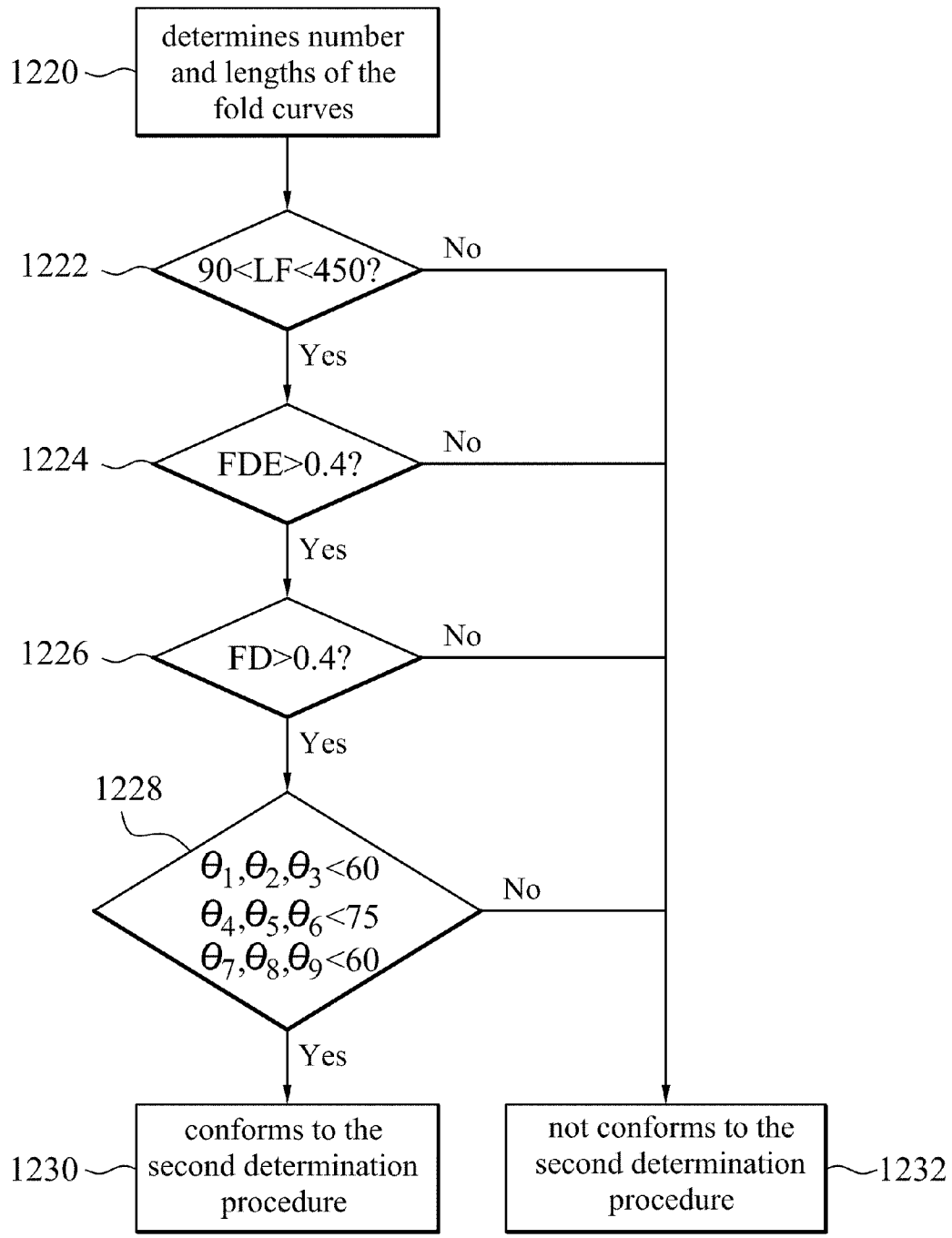
FIG. 7 is a flowchart illustrating steps of performing a second determination procedure of the endoscopic navigation method of the present invention.

In step 122, the second determination procedure is performed to identify fold curves. Referring to the flowchart of FIG. 7. It is first determined whether the fold curves are within a predetermined length range. In the embodiment, the predetermined length range is set as 90-450 units. That is, when a fold curve length LF is not within the predetermined length range, the second determination procedure is determined to not be conformable, and then the fold curve is determined as being invalid. If the determined length range is determined as being conformable, it is further determined whether a ratio (FDE) of pixels of the fold curve with hue values within a predetermined hue value range is larger than a predetermined pixel number. In the embodiment, the predetermined hue value range is smaller than 0.01 unit and larger than 0.1 unit. The predetermined pixel number ratio is set at 0.4. That is, when the pixels of the fold curve with hue values is within the range exceed 40% of the fold curve, the fold curve is valid, or the fold curve does not conform to the second determination procedure, the fold curve is determined as being invalid. Next, it is determined whether a ratio (FD) of pixels of the fold curve with luminance value larger than a predetermined luminance value is larger than a predetermined pixel number ratio. In the embodiment, the predetermined luminance value is set at 0.7 unit. That is, when the pixels of the fold curve with luminance larger than 0.7 unit exceed 40% of the fold curve, the fold curve is determined as being valid; or invalid due to violation of the second determination procedure.

Figure 8A:
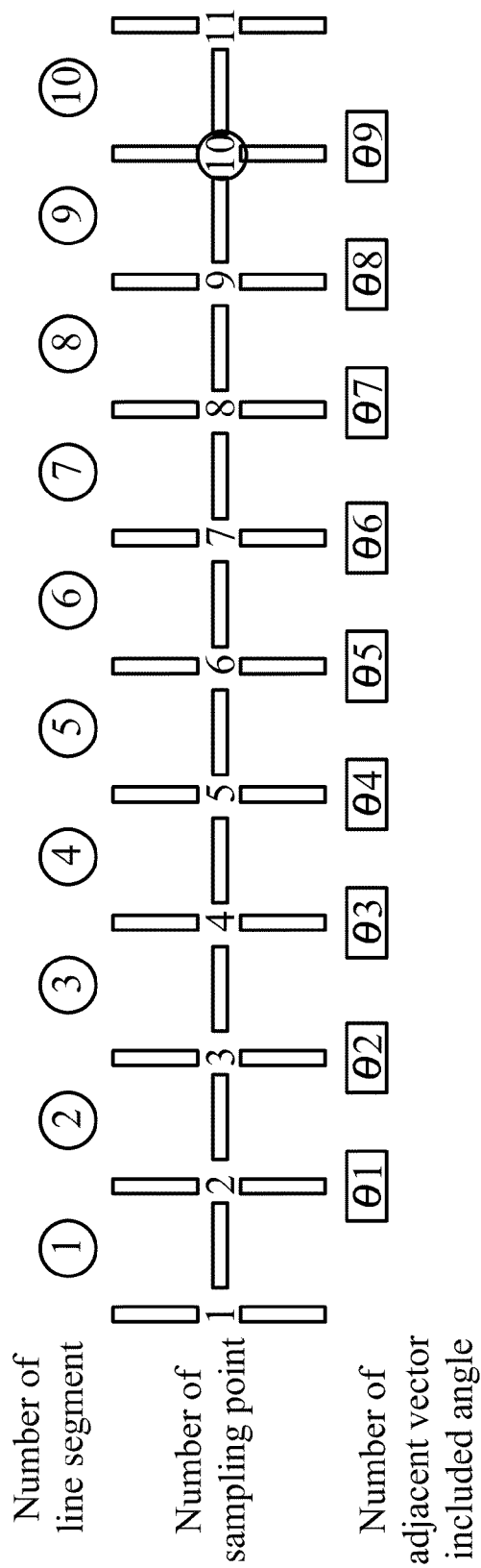
FIG. 8A is a diagram showing determination of an arc shape fold curve according to vector included angels by dividing a fold curve.
Figure 8C:
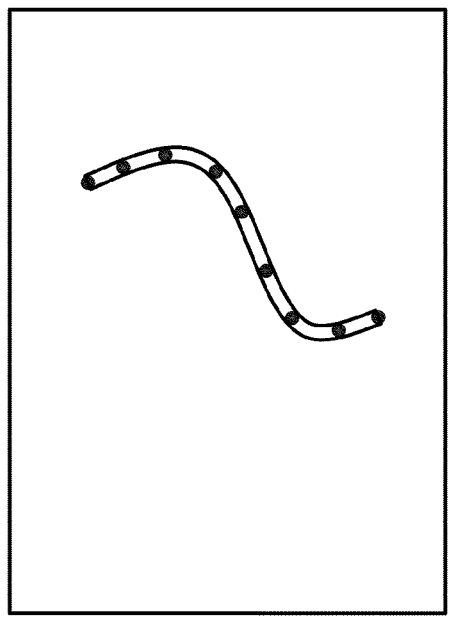
FIG. 8C is an non-arc shape fold curve that does not conform with conditions in an embodiment of the present invention.
Figure 8B:
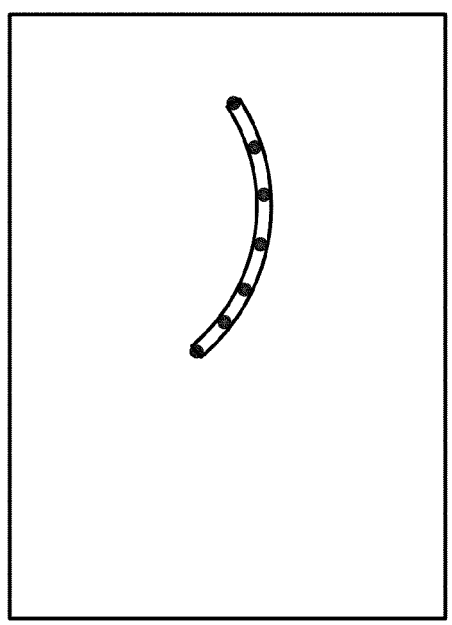
FIG. 8B is an arc shape fold curve that conforms with conditions in an embodiment of the present invention.

Next, it is determined whether the fold curve is conformable to a preset arc shape fold curve. The determination should refer to included angles between two vectors. As an example, the fold curve is divided into ten equal parts. Two adjacent points form a vector, two adjacent vector included angles can be used to determine whether the curve is bent too much or not. Therefore, in this example, there are nine vector included angles. A predetermined vector included angle value is respectively set for each vector included angle. When the all vector included angles are larger than the all predetermined vector included angle values, the fold curve is not an arc shape; or the fold curve is classified as an arc shape fold curve. In the embodiment, as FIG. 8A shows, the fold curve is segmented with serial numbers. The predetermined included angle corresponding to the vector included angles θ1-θ3 and θ7-θ9 is set as 60 degrees, and the predetermined included angle corresponding to the vector included angles θ4-θ6 is set as 75 degrees. That is, when the vector included angles θ1-θ3 and θ7-θ9 of the fold curve is larger than 60 degrees and the vector included angles θ4-θ6 is larger than 75 degrees, then the fold curve is determined to be an arc shape fold curve. The fold curve in the FIG. 8B is an arc shape fold curve, and the fold curve in the FIG. 8C is not an arc shape fold curve. When the fold curve is also an arc shape fold curve, conformation of the second determination is guaranteed and step 126 is performed.

Figure 9A:
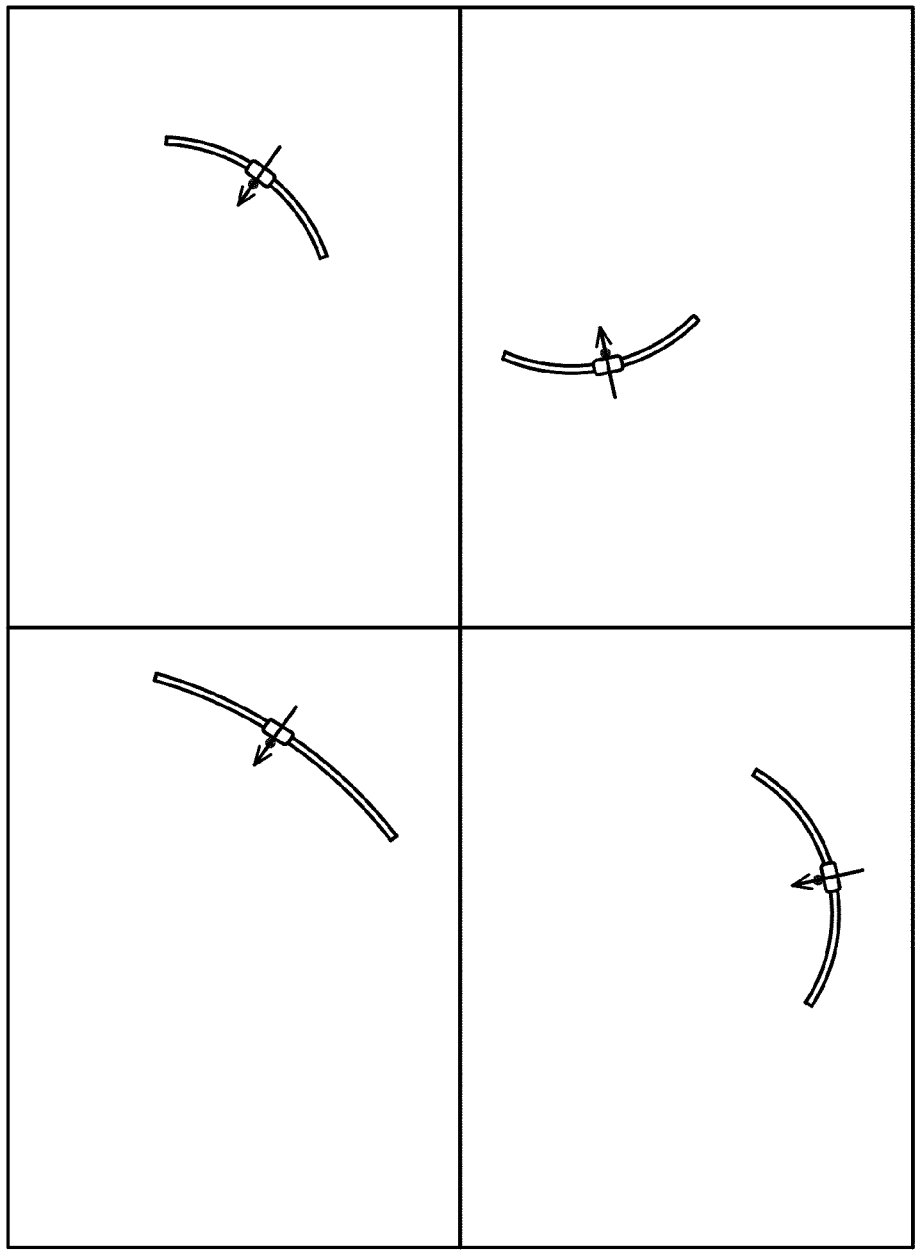
FIG. 9A is an image that conforms with the second determination procedure having indicative symbols in an embodiment of the present invention.
Figure 9B:
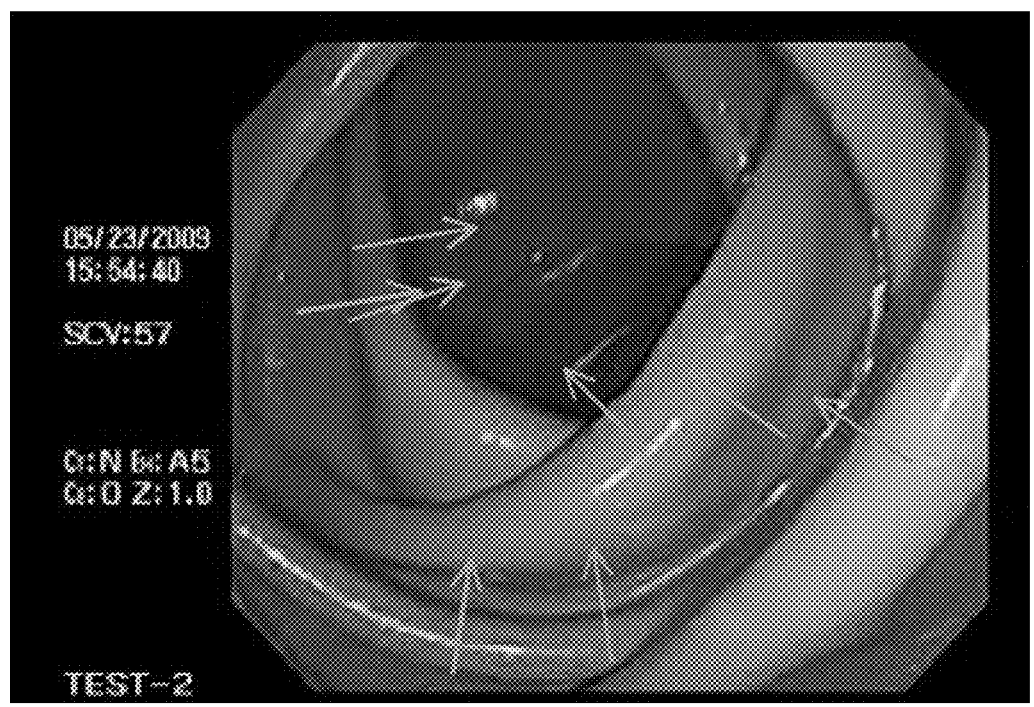
FIG. 9B is a second result image with indicative symbols in an embodiment of the present invention.

In step 126, the second result image indicating lumen direction is produced. The opening direction of a fold curve is determined according to the geometrical center of the fold curve and the midpoint of the line. Usually, the direction vertical to the fold curve is the direction of the lumen region. Therefore, in order to display a correct indication such as an arrow, in the embodiment, the arrow indicating direction is generated referring to the geometrical center and midpoint of the fold curve as FIG. 9A shows. The position and the direction of the indicative symbol are mapped to the original image, and then the result is formed with indicative directions, as FIG. 9B shows. The point direction is the lumen region. Finally, in step 128, the result image is output to the display device to assist users in operating the camera in the lumen.

Figure 10:
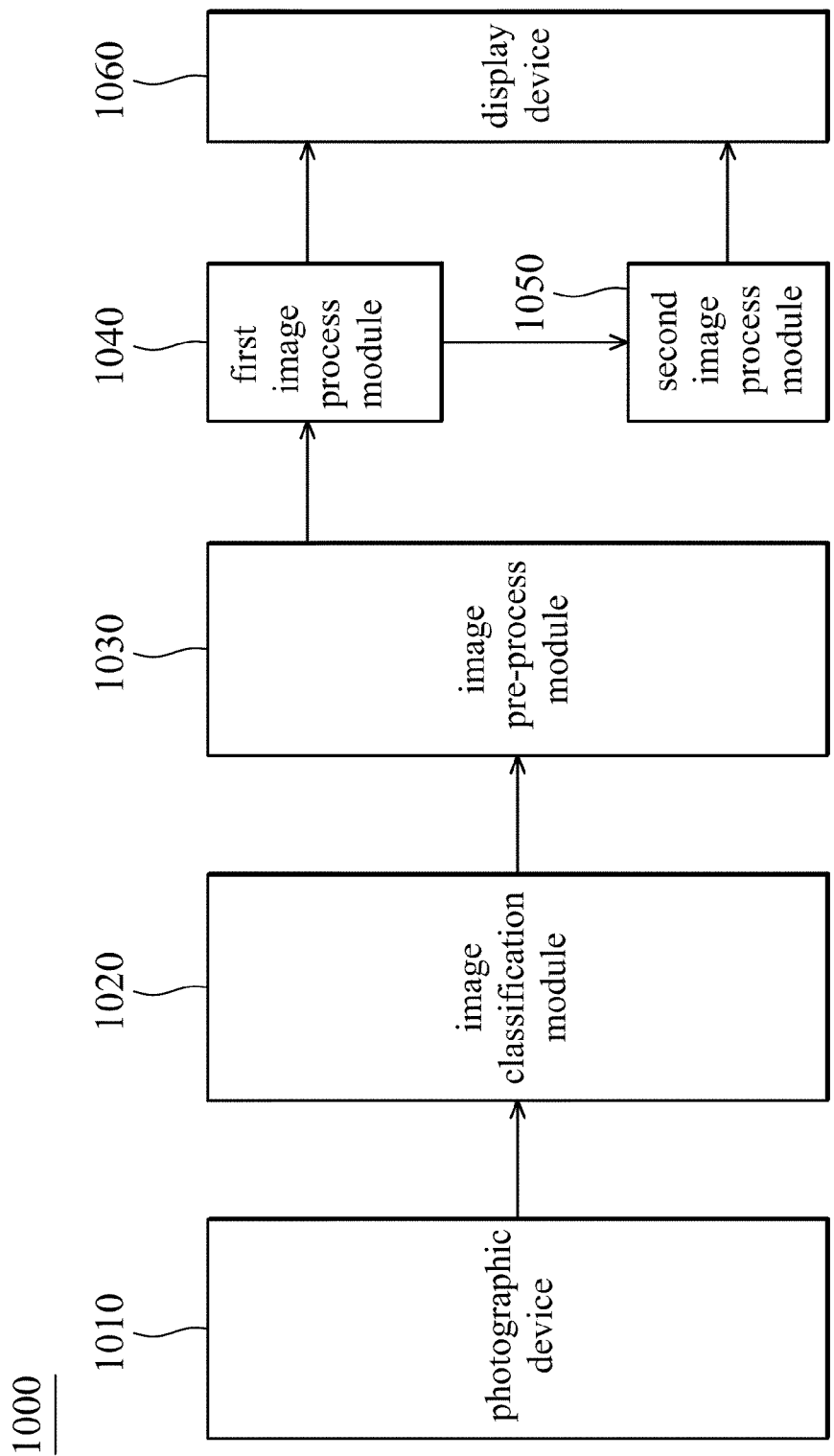
FIG. 10 is a diagram showing the structure of an endoscopic navigation system of the present invention.

FIG. 10 is a diagram showing the structure of an endoscopic navigation system 1000 of the present invention. The endoscopic navigation system 1000 includes a photographic device 1010, an image classification module 1020, an image pre-process module 1030, a first image process module 1040, a second image process module 1050 and a display device 1060. The image classification module 1020, the image pre-process module 1030, the first image process module 1040 and the second image process module 1050 may be integrated into an integrated circuit such as a chipset or a microprocessor.

The photographic device 1010 such as a micro charge-coupled device is used to receive the images, such as colon images from a patient. The image classification module 1020 is used to retrieve the images of the lumen received by the photographic device and perform image classification to determine whether the images are useable or not. The image pre-process module 1030 is used to perform gray-level transformation, median and average filtering and masking on the images.

The first image process module 1030 performs a first image process on the images to filter out dark area(s) of each image to generate a first processed image, and further performs a first determination procedure to identify the dark area(s) of each first processed image. A first result image is produced indicating lumen direction according to the dark area(s). The first determination procedure includes two parts. The first part is to determine whether the first processed image has a dark area, whether boundary pixel number of the dark area is smaller than a predetermined pixel number, whether a ratio of the dark area to the first processed image area is within a predetermined ratio range, and whether a ratio of the pixels of the dark area with hue values within a predetermined hue value range to the dark area is smaller than a predetermined hue area ratio. The second part is to determined whether the first processed image has at least two dark area, whether boundary pixel number of the dark areas is smaller than a predetermined pixel number, whether the included angel between the first largest dark area and the second largest area is smaller than a predetermined angle, whether a ratio of the second largest dark area to the first dark area is smaller than a predetermined ratio value, a ratio of the dark area to the first processed image area is within a predetermined ratio range and whether a ratio of the pixels of the dark areas with hue values within a predetermined hue value range to the dark areas is smaller than a predetermined hue area ratio.

The second image process module 1050 performs a second image process on the image to produce a second processed image, and further performs a second determination procedure to filter out fold curves of the image to identify the fold curves of the second processed image and produce a second result image indicating lumen direction according to the fold curves. The second determination procedure is used to determine whether the fold curves are within a predetermined length range, whether number of the pixels of the fold curves with hue values within a predetermined hue value range is larger than a predetermined pixel number, whether number of the pixels of the fold curve with luminance larger than a predetermined luminance value is larger than a predetermined pixel number and whether the fold curves are as an arc shape fold curve.

The display device 1060 is used to display the first result image or the second result image to assist users in operating the photographic device 1010 in the lumen. When the lumen region is pointed out by the first image process module 1040, wherein a first result image indicating lumen direction is generated, the image may not be sent to the second image processes module 1050. The first result image is output to the display device 1060. If the first image process module can't identify the lumen region, the image is delivered to the second image process module for fold curve identification. If the lumen region is pointed out by the second image process module 1050, then the second result image is output to the display device 1060.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An endoscopic navigation method, comprising the steps of:
   receiving an image from a photographic device of an endoscopic navigation system in a lumen;
   performing image classification to determine whether the image is usable, wherein determining the image class comprises:

when a ratio of pixels of the image with luminance values smaller than a first predetermined luminance value to the image size, is larger than a predetermined ratio value, the image is classified as a very dark image;

when a ratio of pixels of the image with luminance values larger than a second predetermined luminance value to the image size, is larger than the predetermined ratio value, the image is classified as a very bright image;

when a ratio of pixels of the image with hue values smaller than a first predetermined hue value or larger than a second predetermined hue value and saturation values larger than a predetermined saturation value to the image size, is larger than the predetermined ratio value, the image is classified as a double-exposure image; and when the image is not classified as a very dark image, a very bright image or a double-exposure image, the image is classified as a clear image;

performing a first image process on the image to filter out dark areas of the image to produce a first processed image;

performing a first determination procedure to identify the dark areas of the first processed image;

producing a first result image for indicating lumen direction;

performing a second image process to filter out fold curves of the image to produce a second processed image when there is no dark area in the image;

performing a second determination procedure to identify the fold curves of the second processed image;

producing a second result image for indicating lumen direction according to the fold curves;

outputting the first result image or the second result image to a display device in the endoscopic navigation system to assist a user in operating the photographic device in the lumen.

2. The method as claimed in claim 1, wherein performing image classification comprises:
 determining the image class according to parameters of the image attributed to a specified color space,
 wherein when the image is classified as a clear image, the image is usable.

3. The method as claimed in claim 1, further comprising performing an image pre-process on the usable image.

4. The method as claimed in claim 3, wherein performing the image pre-process on the usable image comprises:
 performing gray-level transformation, median and average filtering and masking on the image.

5. The method as claimed in claim 1, wherein performing the first image process comprises:
 performing binarization, labeling filtering and median filtering on the image; and
 determining a number of dark areas of the image.

6. The method as claimed in claim 1, wherein performing the first determination procedure comprises:
 determining whether the first processed image has a dark area;
 determining whether the boundary pixel number of the dark area is smaller than a predetermined pixel number;
 determining whether a ratio of the dark area to the first processed image area is within a predetermined ratio range; and
 determining whether a ratio of a portion of the dark areas with hue values within a predetermined hue value range to the dark area, is smaller than a predetermined hue area ratio.

7. The method as claimed in claim 1, wherein performing the first determination procedure comprises:
 determining whether the first processed image has at least two dark areas;
 determining whether a boundary pixel number of the dark areas is smaller than a predetermined pixel number;
 determining whether an included angle between the first large dark area and the second large dark area in the processed image is smaller than a predetermined angle;
 determining whether a ratio of the second large area to the first large dark area is smaller than a predetermined ratio value;
 determining whether a ratio of the dark areas to the first processed image area is within a predetermined ratio range; and
 determining whether a ratio of a portion of the dark areas with hue values within a predetermined hue value range to the dark areas is smaller than a predetermined hue area ratio.

8. The method as claimed in claim 1, wherein producing the first result image for indicating lumen direction comprises:
 producing indicative symbols on the image according to the geometrical center of the largest dark area and the geometrical center of the first processed image to form the first result image.

9. The method as claimed in claim 1, wherein performing the second image process comprises:
 performing Laplace filtering, boundary detection, boundary masking and labeling filtering; and
 determining a number and lengths of the fold curves in the image.

10. The method as claimed in claim 1, wherein performing the second determination procedure comprises:
 determining whether the fold curves are within a predetermined length range;
 determining whether a ratio of pixels of each fold curve with hue values within a predetermined hue value range to a respective fold curve, is larger than a predetermined pixel number ratio;
 determining whether a ratio of pixels of each fold curve with luminance values larger than a predetermined luminance value, is larger than the predetermined pixel number ratio; and
 determining whether the fold curves conform to a preset arc shape fold curve.

11. The method as claimed in claim 1, wherein producing the second result image for indicating lumen direction comprises:
 producing indicative symbols in the image to form the second result image according to opening directions of the fold curves.

12. The method as claimed in claim 1, wherein producing the second result image for indicating lumen direction comprises:
 producing indicative symbols in the image to form the second result image according to the midpoints and the geometric centers of the fold curves.

13. An endoscopic navigation system, comprising:
 a photographic device configured to photograph a colon interior;
 an image classifying module configured to retrieve an image photographed by the photographic device, and perform image classification to determine whether the image is usable, wherein the image classifying module is configured to perform the steps of:
when a ratio of pixels of the image with luminance values smaller than a first predetermined luminance value to the image size, is larger than a predetermined ratio value, the image is classified as a very dark image;
when a ratio of pixels of the image with luminance values larger than a second predetermined luminance value to the image size, is larger than the predetermined ratio value, the image is classified as a very bright image;
when a ratio of pixels of the image with hue values smaller than a first predetermined hue value or larger than a second predetermined hue value and saturation values larger than a predetermined saturation value to the image size, is larger than the predetermined ratio value, the image is classified as a double-exposure image; and
when the image is not classified as a very dark image, a very bright image or a double-exposure image, the image is classified as a clear image;
a first image process module configured to perform a first image process on the image to filter out dark areas of the image to produce a first processed image, perform a first determination procedure to identify the dark areas of the first processed image, and produce a first result image for indicating lumen direction according to the dark areas;
a second image processing module configured to perform a second image process on the image to produce a second processed image, perform a second determination procedure to filter out fold curves to identify the fold curves of the second processed image and produce a second result image for indicating lumen direction according to the fold curves; and
a display device configured to display the first result image or the second result image to assist a user in operating the photographic device in the lumen.

14. The system as claimed in claim 13, further comprising an image pre-process module configured to perform gray-level transformation, median and average filtering and masking on the image.

15. The system as claimed in claim 13, wherein the first determination procedure comprises determining:
whether the first processed image has a dark area;
whether a boundary pixel number of the dark area is smaller than a predetermined pixel number;
whether a ratio of the dark area to the first processed image area is within a predetermined ratio range; and
whether a ratio of a portion of dark areas with hue values within a predetermined hue value range to the dark area, is smaller than a predetermined hue area ratio.

16. The system as claimed in claim 13, wherein the first determination procedure comprises determining:
whether the first processed image has at least two dark areas;
whether a boundary pixel number of the dark areas is smaller than a predetermined pixel number;
whether an included angle between the first largest dark area and the second largest dark area in the processed image is smaller than a predetermined angle;
whether a ratio of the second largest dark area to the first largest dark area is smaller than a predetermined ratio;
whether a ratio of the dark areas to the first processed image area is within a predetermined ratio range; and
whether a ratio of a portion of dark areas with hue values within a predetermined hue value range to the dark areas, is smaller than a predetermined hue area ratio.

17. The system as claimed in claim 13, wherein the second determination procedure comprises determining:
whether the fold curves are within a predetermined length range;
whether a ratio of pixels of each fold curve with hue values within a predetermined hue value range to a respective fold curve, is larger than a predetermined pixel number ratio;
whether a ratio of pixels of each fold curve with luminance values larger than a predetermined luminance value to a respective fold curve, is larger than the predetermined pixel number ratio; and
whether the fold curves conform to a preset arc shape fold curve.

* * * * *